United States Patent [19]
Luce

[11] Patent Number: 5,954,645
[45] Date of Patent: Sep. 21, 1999

[54] APPLANATION DETECTION SYSTEM FOR A NON-CONTACT TONOMETER

[75] Inventor: David A. Luce, Clarence Center, N.Y.

[73] Assignee: Leica Microsystems Inc., Depew, N.Y.

[21] Appl. No.: 09/054,723

[22] Filed: Apr. 3, 1998

[51] Int. Cl.[6] .................................................... A61B 3/16
[52] U.S. Cl. ........................ 600/401; 600/399; 600/405; 351/212
[58] Field of Search ................................. 600/398, 399, 600/401, 405; 351/208, 210, 212

[56] References Cited

U.S. PATENT DOCUMENTS

| 3,585,849 | 6/1971 | Grolman | 600/401 |
| 3,882,718 | 5/1975 | Kriebel | 600/401 |
| 4,665,923 | 5/1987 | Kobayashi | 600/401 |
| 4,724,843 | 2/1988 | Fisher | 600/401 |
| 4,878,750 | 11/1989 | Sekiguchi | 351/212 |
| 5,283,598 | 2/1994 | McMillan et al. | 351/212 |
| 5,636,635 | 6/1997 | Massie et al. | 600/405 |
| 5,754,273 | 5/1998 | Luce | 351/212 |
| 5,830,139 | 11/1998 | Abreu | 600/405 |
| 5,865,742 | 2/1999 | Massie | 600/405 |

Primary Examiner—Cary O'Connor
Assistant Examiner—Charles Marmor, II
Attorney, Agent, or Firm—Simpson, Simpson & Snyder

[57] ABSTRACT

A non-contact tonometer is improved by providing a non-telecentric applanation detection system enabling relaxation of instrument alignment requirements during testing. In a preferred embodiment, the applanation detection system comprises an emitter for directing an obliquely incident beam of light for reflection by the cornea, and a detector array having a plurality of photosensitive detector array elements located to receive corneally reflected light. The detector array generates a plurality of signal curves for light energy received at different locations on the array as a function of time, and the signal curves are evaluated to determine an optimal signal curve which best indicates the moment of applanation.

13 Claims, 7 Drawing Sheets

VOLTAGE

APPLANATION

TIME

Fig. 3
PRIOR ART

VOLTAGE

TIME

APPLANATION DETECTION SYSTEM FOR A NON-CONTACT TONOMETER

BACKGROUND

A. Field of the Invention

The present invention relates generally to the field of non-contact tonometry, and more particularly to a non-contact tonometer employing an improved applanation detection system which increases measurement reliability by making the instrument less sensitive to alignment variations.

B. Description of the Prior Art

In the operation of known non-contact tonometers for measuring intraocular pressure (IOP) of a patient's eye, an increasing force air pulse is discharged through a pump-fed nozzle along a test axis toward the eye to deform the cornea from a state of convexity, through an instantaneous state of "applanation" wherein a predetermined area of the cornea is flattened, to a state of concavity; the cornea is then allowed to return to its original convex state under natural forces. Opto-electronic means are used to continuously monitor the corneal deformation and thereby determine the moment of applanation. The interval of time or pump plenum pressure required to achieve applanation is then used as a correlate of IOP.

Figure 1A:
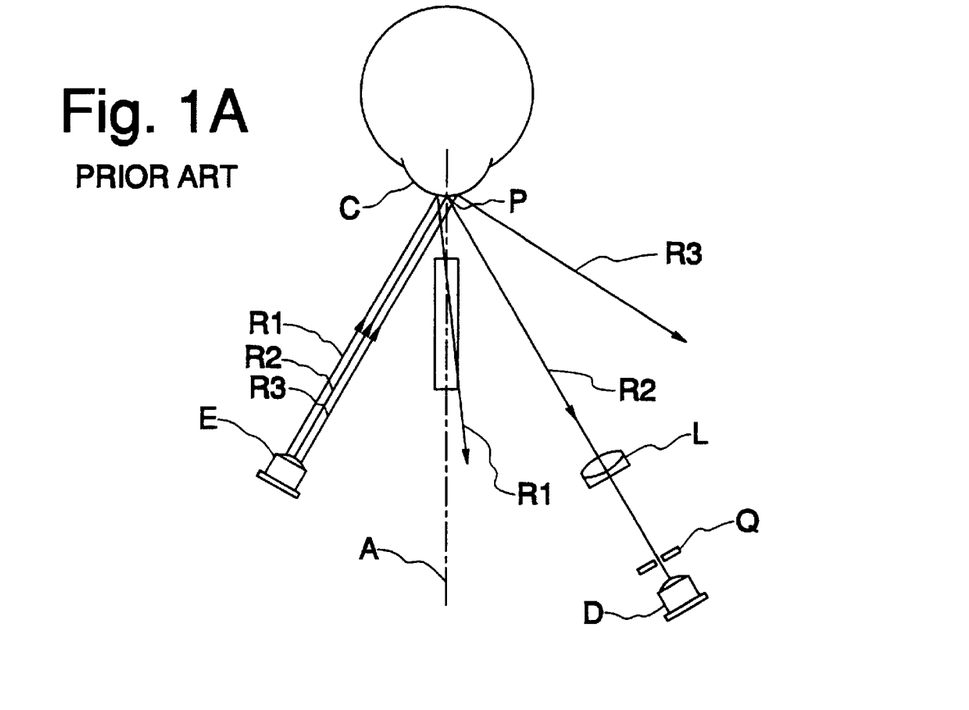
FIGS. 1A and 1B are schematic diagrams showing operation of a telecentric applanation detection system of the prior art.
Figure 1B:
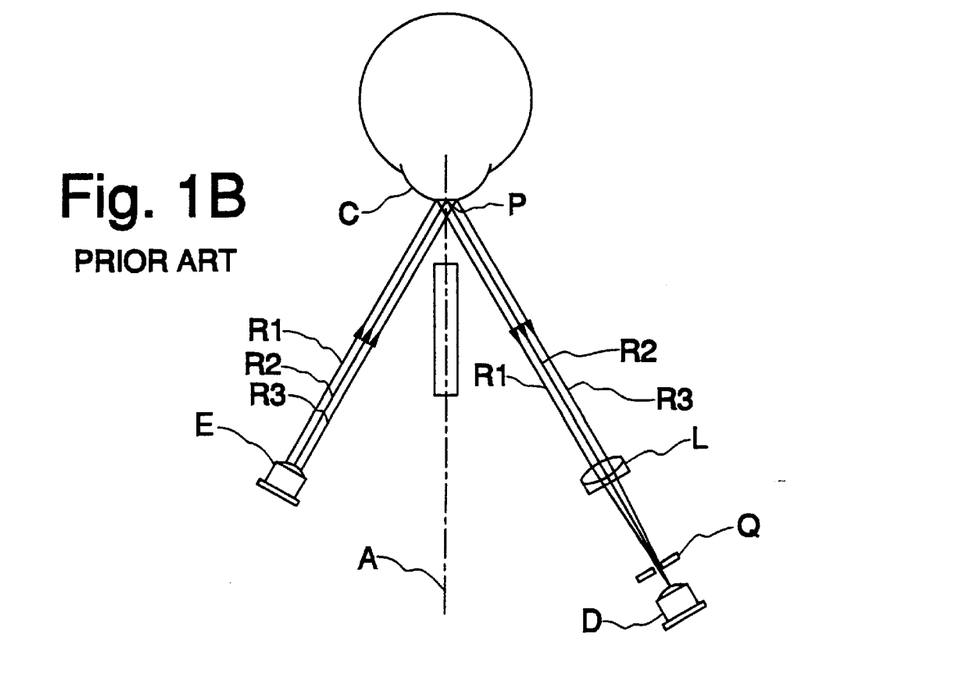

Heretofore, applanation detection systems used in non-contact tonometers have been telecentric in nature, requiring precise three-dimensional alignment of the discharge nozzle relative to the cornea. For example, the XPERT® NCT manufactured by Reichert Ophthalmic Instruments, a division of Leica Inc., assignee of the present application, currently employs a telecentric applanation detection system as shown in FIGS. 1A and 1B. An emitter E directs an incident beam of light represented by parallel rays R1, R2, and R3 at an oblique angle toward corneal pole C. A single photo-detector D, which is positioned at a symmetrically equal and opposite angle behind a pinhole aperture A in the focal plane of a collector lens L, receives a small bundle of corneally reflected rays. When the cornea is in its normal convex state, as shown in FIG. 1A, the fan-shaped dispersion of rays R1–R3 results in a weak detection signal. As the cornea is progressively transfigured toward a state of applanation by the fluid pulse, the fan-shaped configuration of dispersed rays closes and the detector signal becomes stronger. When applanation occurs according to FIG. 1B, dispersion of rays R1–R3 is at a minimum, resulting in a peak signal at detector D.

Figure 2:
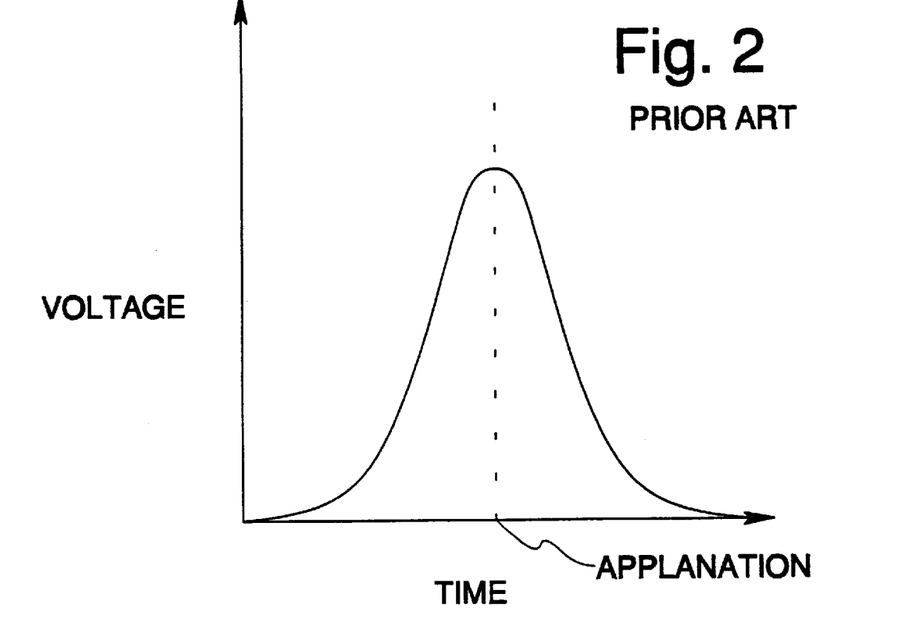
FIG. 2 is a plot, taken from the prior art, showing applanation detector signal versus time for a tonometer measurement made with proper instrument alignment.
Figure 3:
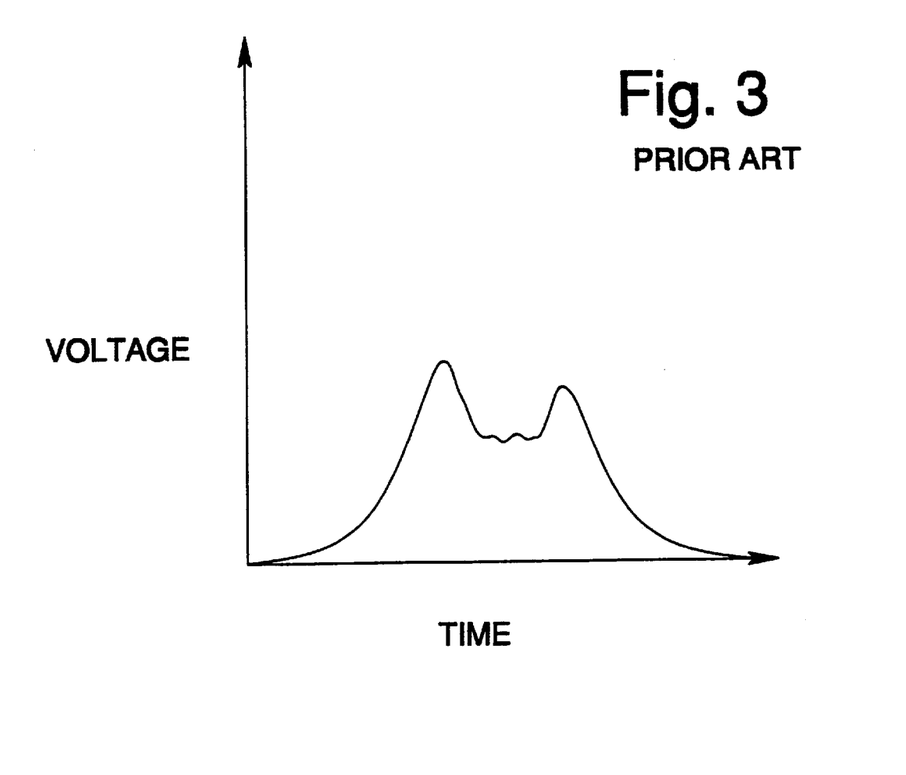
FIG. 3 is a plot similar to that of FIG. 2, however for a tonometer measurement made with improper instrument alignment.

As may be appreciated, the telecentric system described above is extremely sensitive to misalignment of the instrument with respect to the cornea. FIG. 2 includes a plot of a typical detector signal as a function of time in a properly aligned instrument, and FIG. 3 includes a similar plot in a misaligned instrument. The undesirable consequence of misalignment is a false reading of an early signal peak, which will yield an inaccurate IOP measurement that is usually lower than actual IOP. Since an important reason for subjecting the patient to IOP measurement is to detect elevated IOP, an indication of glaucoma, falsely low IOP measurements due to misalignment are a serious and recognized problem. In view of this, a large portion of the cost of a commercially available non-contact tonometers is attributed to the expensive opto-electronic alignment system necessary for precise alignment. In the XPERT® NCT discussed above, the applanation detection system imposes stringent alignment requirements on the order of $\Delta X \leq 0.05$ mm, $\Delta Y \leq 0.05$ mm, and $\Delta Z \leq 0.3$ mm, where X is side-to-side, Y is vertical, and Z is distance from the patient.

It is further noted that efforts to relax alignment precision requirements by providing a larger pinhole aperture at the detector are not helpful because signal resolution is lost, once again making it impossible to accurately determine the moment of applanation with certainty.

SUMMARY OF THE INVENTION

Therefore, it is an object of the present invention to improve a non-contact tonometer by providing an applanation detection system which gives greater measurement accuracy and precision despite variations in instrument alignment from an ideal alignment condition.

In a preferred embodiment of the present invention, applanation detection is carried out by an infra-red emitter in cooperation with a light-sensitive detector array. The emitter is positioned to direct an oblique beam of collimated light for reflection by the patient's cornea, and the detector array is located behind a beam contractor and an aperture-lens array at a symmetrically opposite angle to the emitter for receiving the corneally reflected rays. At the moment when applanation occurs due to an incident air pulse, dispersion of corneally reflected rays will be at a minimum and a peak signal will be generated by one of the detector array elements depending upon alignment conditions. The signal information from each detector array element is evaluated as a function of time to determine an optimal signal curve from the detector array element best located under the alignment conditions to receive the concentrated light energy. Signals from adjacent detector array elements may be summed and evaluated along with signal curves from each individual array element to account for situations where the concentration of light falls on a boundary between array elements, providing better measurement resolution.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 4:
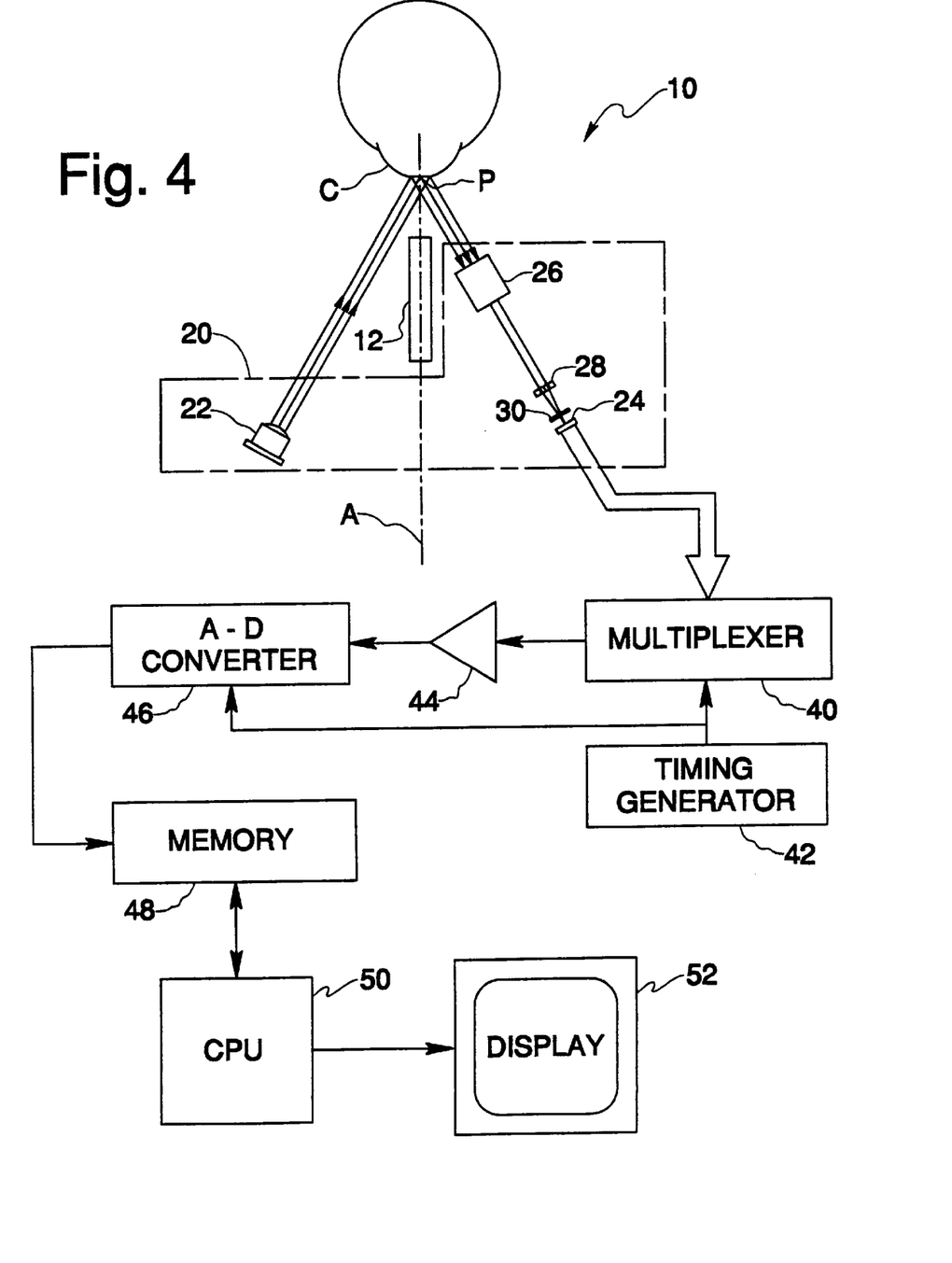
FIG. 4 is a schematic diagram showing an applanation detection system formed in accordance with a first embodiment of the present invention.

Referring now to FIG. 4 of the drawings, there is shown schematically a non-contact tonometer 10 for measuring IOP of a cornea C. Non-contact tonometer 10 is conventional in that it includes a fluid discharge nozzle 12 aligned with cornea C along a test axis A. Nozzle 12 cooperates with a motorized pump mechanism (not shown) in flow communication therewith to generate and discharge a fluid pulse of increasing force toward a corneal pole P defined by the intersection of test axis A with the surface of cornea C, as is well known in the art of non-contact tonometry. The fluid pulse acts to progressively deform cornea C from a state of convexity through a state of applanation, as described above in connection with PRIOR ART FIGS. 1A and 1B.

In accordance with a first embodiment of the present invention, non-contact tonometer 10 includes novel applanation detection means, generally identified by the reference numeral 20, for monitoring corneal deformation caused by an incident fluid pulse. Applanation detection means 20 is novel because it is a non-telecentric system utilizing a detector array 24 for receiving corneally reflected light, as opposed to a telecentric system utilizing a collector lens, a pin-hole aperture in the lens' focal plane, and a single detector element for receiving corneally reflected light. As will be apparent from the coming description, the non-telecentric system of the present invention permits instrument alignment requirements to be relaxed without sacrificing measurement accuracy. Applanation detection means 20 may be housed in optical grade plastic or mounted on a test portion of the instrument to be free standing in air.

An infra-red emitter 22 is positioned on one side of test axis A for directing an oblique, collimated beam of light approximately 3 mm in diameter toward cornea C, and more precisely toward corneal pole P, for reflection by the corneal surface. Light rays from emitter 22 are "fanned out" or dispersed upon reflection by the curved corneal surface; however, dispersion of the corneally reflected rays is at a minimum at the moment applanation, as discussed above. It is the function of detector array 24 to measure light reflected by the cornea for determination of a peak measurement corresponding to applanation.

Figure 5:
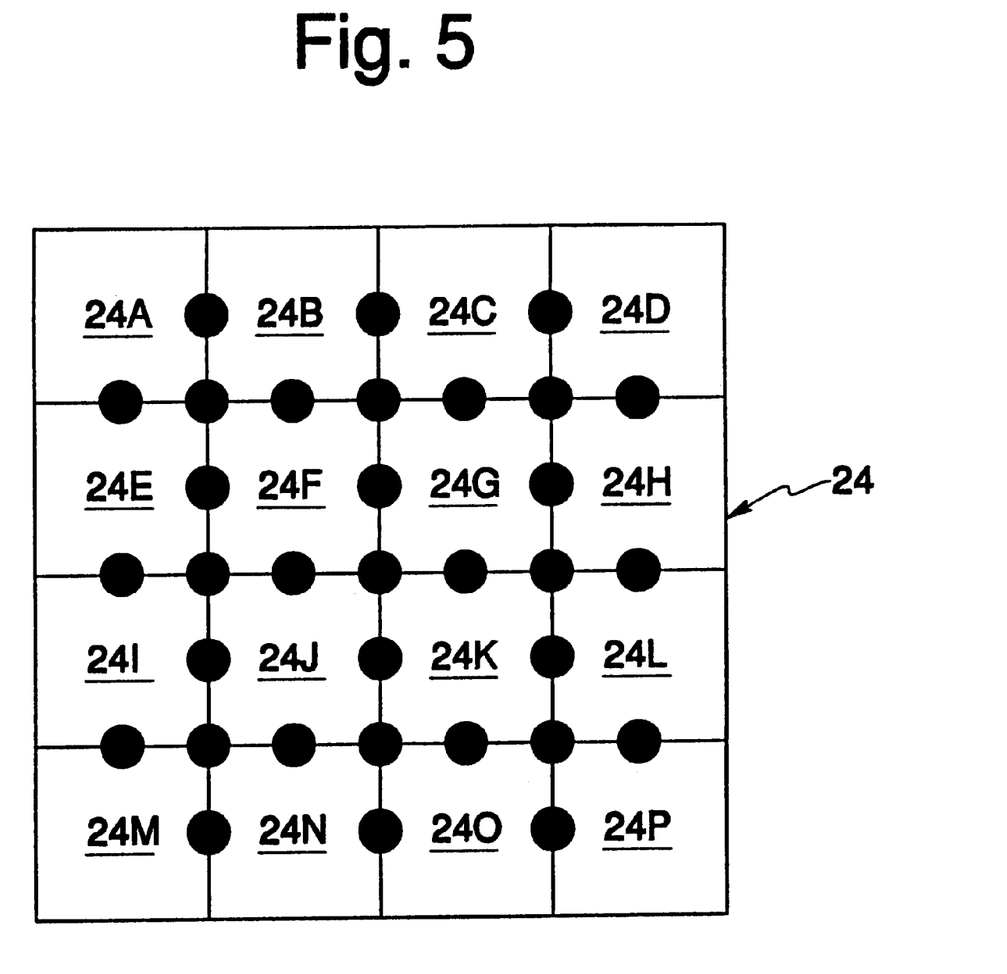
FIG. 5 is a view showing a detector array surface of the detector array shown in FIG. 4.

In the preferred embodiments, detector array 24 is a four-by-four area array having sixteen photodiode elements 24A–24P on its detector surface, as shown in FIG. 5. Detector array 24 is orientated in angular symmetry with emitter 22 about test axis A, with its detector surface facing cornea C to receive light rays reflected by the corneal surface. Detector array 24 is preferably a silicon photodiode area array of a type manufactured by Hamamatsu Photonics K.K. having high spectral sensitivity in the infra-red range, however a CCD or other suitable area detector may be used in practicing the present invention. The presently indicated size of each photodiode element 24A–24P is approximately 1 mm square, whereby the entire detector array 24 is approximately 4 mm square. Since the detector array includes sixteen detector elements 24A–24P each capable of detecting radiant power from corneally reflected light at a unique location during deformation of cornea C, the need of the prior art to carefully control the location of the radiant power peak through precise X, Y, and Z alignment of test axis A and discharge nozzle 12 relative to corneal pole P is substantially reduced. More specifically, the present invention dictates alignment ranges of $\Delta X \leq 1.0$ mm, $\Delta X \leq 1.0$ mm, and $\Delta Z \leq 2.0$ mm, where X is side-to-side, Y is vertical, and Z is distance from the patient. This offers a considerable improvement over the alignment requirements of the prior art instrument mentioned in the above background.

Figure 6:
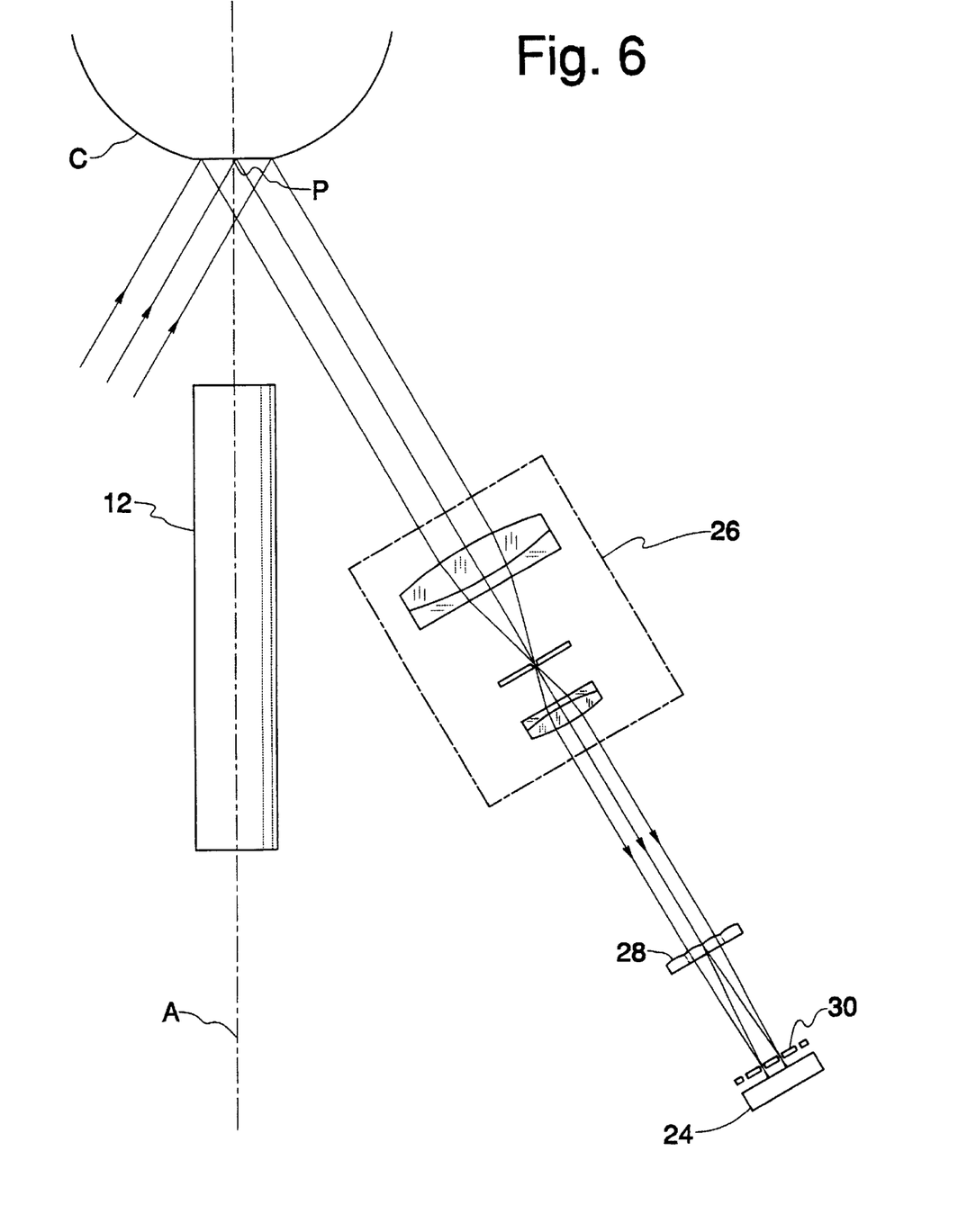
FIG. 6 is an enlarged optical schematic showing passage of a corneally reflected beam through a beam contractor, pinhole aperture array, and lens array to reach the detector array surface.

In order to provide a scaling function on the detector side of cornea C, a beam expander 26 is aligned with detector array 24 in reverse orientation such that it acts as a "beam contractor". Referring to FIG. 6, beam contractor 26 reduces the cross-sectional area of the corneally reflected beam by a scaling factor appropriate for the size of detector array 24.

A lens array 28 and an associated pinhole aperture array 30 are preferably aligned in the scaled beam path in front of detector array 24 to improve the time resolution of the system. Lens array 28 includes a plurality of lens elements arranged in an array configuration corresponding to the configuration of detector elements 24A–24P making up detector array 24, i.e. a four-by-four configuration. Likewise, aperture array 30 includes a plurality of individual pinhole apertures arranged in corresponding configuration. The lens array elements and associated pinhole apertures cooperate to provide sharper signal curves at the detector array elements, such that the time when a peak signal is received by a given detector element may be determined more precisely.

Figure 7A:
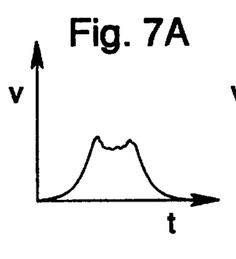
FIGS. 7A–7P are plots showing applanation detector signal versus time for the respective detector array elements 24A–24P for a measurement made with an arbitrary alignment condition within a working alignment range of the present invention.
Figure 7B:
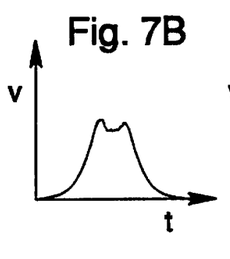
Figure 7C:
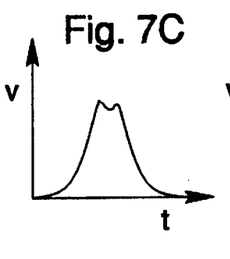
Figure 7D:
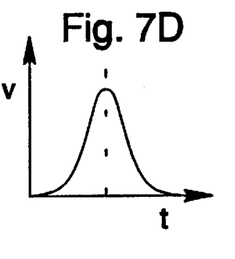
Figure 7E:
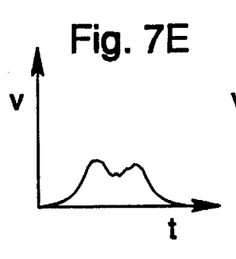
Figure 7F:
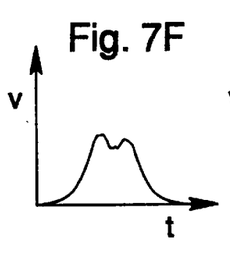
Figure 7G:
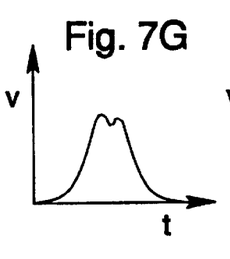
Figure 7H:
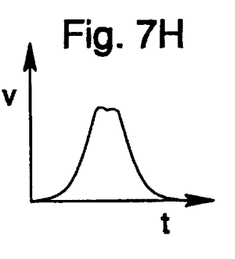
Figure 7I:
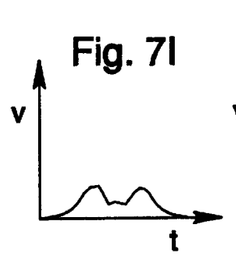
Figure 7J:
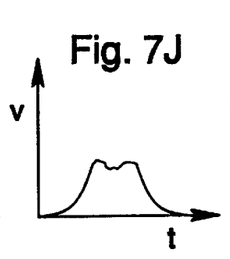
Figure 7K:
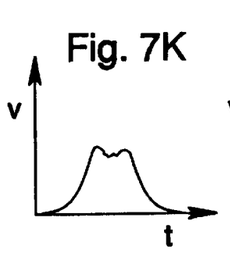
Figure 7L:
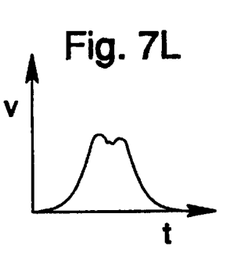
Figure 7M:
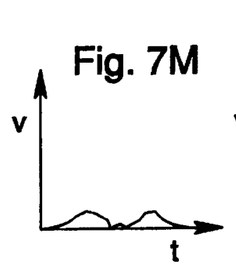
Figure 7N:
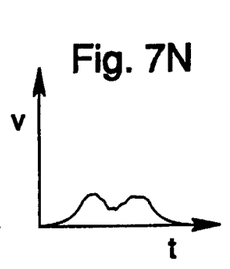
Figure 7O:
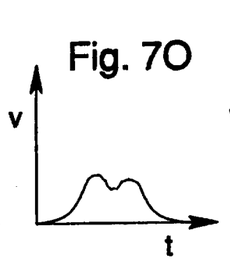
Figure 7P:
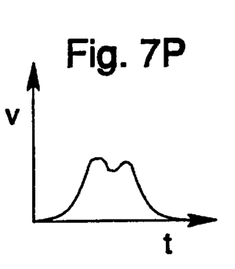

Output from each of the sixteen parallel signal channels of detector array 24 is sampled at a rate of 500 kHz by multiplexer 40 driven by timing generator 42. Sampled signal information indicating radiant power received by the respective detector array elements 24A–24P is amplified by amplifier 44, converted to digital form by A-D converter 46, and stored in memory 48. As a result, sixteen signal curves are stored in memory; each signal curve represents the intensity of light received by detector array 24 at a unique array location as a function of time. FIGS. 7A–7P illustrate typical signal curves generated by detector array elements 24A–24P for an arbitrarily chosen imperfect alignment condition within the tolerated alignment ranges set forth above for the present invention. As may be seen, the signal curve of FIG. 7D exhibits the highest peak, and thus array element 24D corresponds to the location of reflected beam convergence associate with the applanation event. The signal curves of FIGS. 7C, 7G, and 7H from detector array elements 24C, 24G, and 24H, which are adjacent to detector array element 24D, exhibit somewhat lower peaks with diminished resolution as compared with the signal curve from detector array element 24D. Further signal degradation is exhibited as distance from detector array element 24D increases.

The stored signal curves are evaluated by CPU 50 to determine an optimal signal curve having the highest peak. In the above example, the optimal signal curve is that illustrated in FIG. 7D. This optimal signal curve is analyzed to determine the moment of applanation based on the peak signal, as is currently done in prior art instruments having a single detector element generating only one signal curve. The interval of time necessary to achieve applanation, or the pump plenum pressure recorded at the moment of applanation, is then used as a correlate of IOP pursuant to known practice. Where the measurement system is scaled at 128 $\mu$sec per mmHg (units for IOP), the overall sampling rate of 32 $\mu$sec (2 $\mu$sec×16 channels) gives a resolution of 0.25 mmHg.

Since the use of a detector array having a plurality of discreet array elements involves the possibility that the converged beam may straddle a boundary between adjacent array elements, whereby the converged beam strikes from two to four different array elements, evaluation of the signal information preferably accounts for this possibility. FIG. 5 shows dots representing thirty-three different border location possibilities for the incident converged beam on four-by-four detector array 24. For each of these possibilities, a secondary signal curve is generated by adding signals from the involved detector array elements. For example, a secondary signal curve is generated to account for the two-way border between detector array elements 24A and 24B by summing the respective signals from these detector array elements. Likewise, a secondary signal curve is generated to account for the four-way border at the junction of detector array elements 24A, 24B, 24E, and 24F. The thirty-three secondary signal curves may be stored in memory 48 and evaluated by CPU 50 along with the sixteen primary signal curves taken directly from each respective detector array element to determine the optimal signal curve. Display 52 reports measurement output to the operator.

Figure 8:
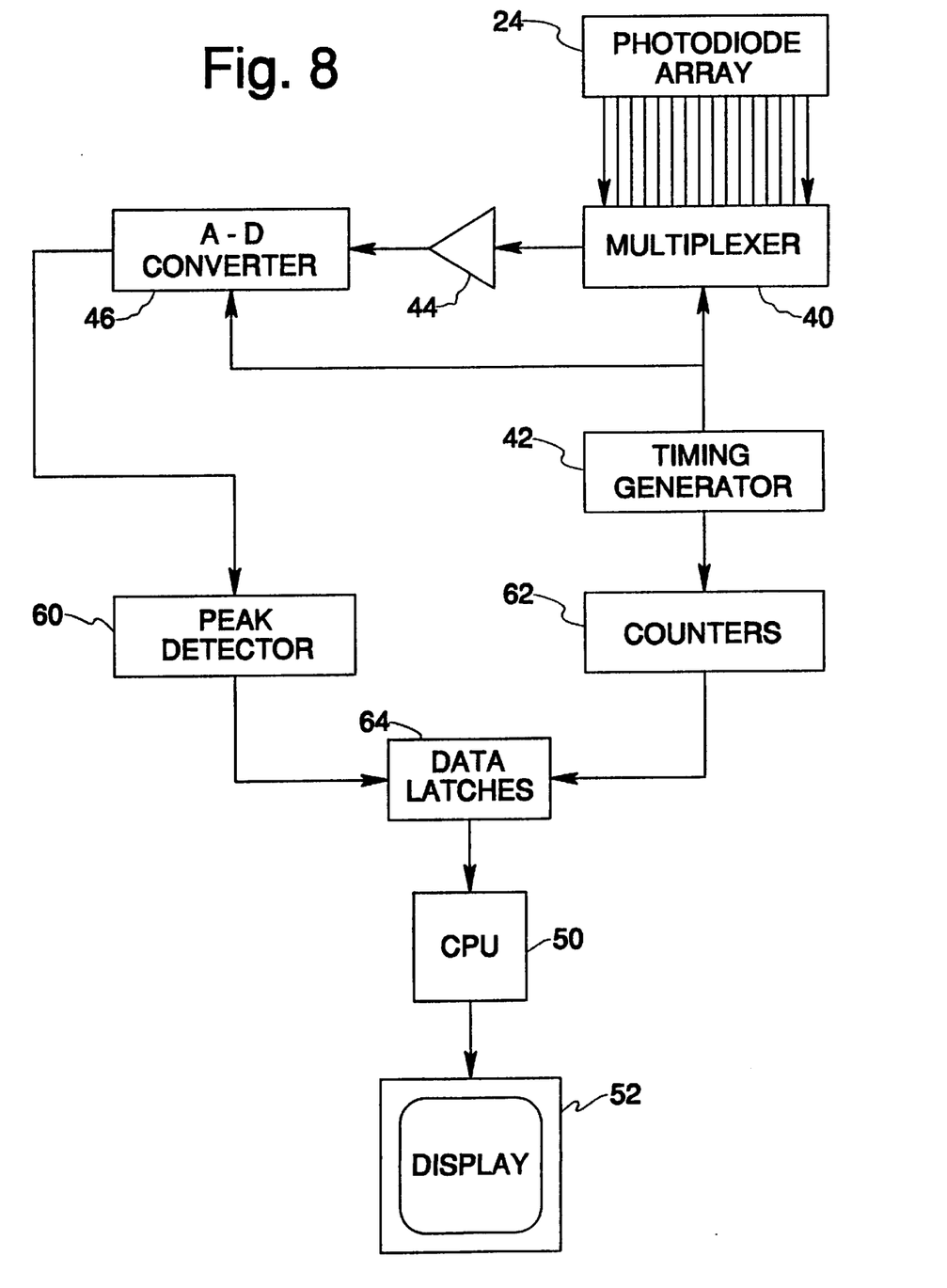
FIG. 8 is a block diagram illustrating evaluation electronics of a second embodiment of the present invention.

As an alternative to storing the signal information in memory for evaluation by CPU 50, real time evaluation of the signal information may be conducted using a peak detector circuit 60 as illustrated in FIG. 8. Signals from timing generator 42 drive counters 62 and the sampling of detector array elements 24A–24P. Each time peak detector 60 indicates a new high signal from a detector array element, the counter and signal data are held by data latches 64. Once a peak signal is determined, i.e. when a subsequent sweep of detector array 24 fails to yield a new peak signal, the peak signal and counter information are evaluated by CPU 50 to determine the time of applanation for correlation to IOP.

What is claimed is:

1. A non-contact tonometer for measuring intraocular pressure of a patient's eye comprising:

a test axis;

fluid pulse means for generating a fluid pulse of increasing force and discharging said fluid pulse along said test axis toward said eye to progressively deform a cornea of said eye to achieve a state of corneal applanation;

applanation detection means for monitoring deformation of said cornea caused by said fluid pulse, said applanation detection means including an emitter on one side of said test axis for directing an incident beam of light to said cornea for reflection by said cornea and a detector array on another side of said test axis, said detector array having a plurality of photosensitive detector array elements for receiving light reflected by said cornea and generating a plurality of primary signal curves representative of the intensity of light received by said detector array at a plurality of different array locations as a function of time; and evaluation means for determining an optimal signal curve from said plurality of primary signal curves and calculating said intraocular pressure from said optimal signal curve.

2. The non-contact tonometer according to claim 1, wherein there is only one said emitter.

3. The non-contact tonometer according to claim 1, wherein said detector array is sampled at a predetermined frequency.

4. The non-contact tonometer according to claim 1, wherein said detector array is a photodiode detector array.

5. The non-contact tonometer according to claim 4, wherein said detector array is a four-by-four array having sixteen photodiode elements.

6. The non-contact tonometer according to claim 1, wherein said evaluation means includes a peak detector circuit for determining said optimal signal curve.

7. The non-contact tonometer according to claim 1, wherein said evaluation means includes memory means for storing said plurality of primary signal curves.

8. The non-contact tonometer according to claim 7, wherein said evaluation means combines said signal curve information from subgroups of adjacent elements in said detector array to provide a plurality of secondary signal curves representative of the intensity of light received by said detector array at a plurality of different border locations on said detector array as a function of time, and said evaluation means determines said optimal signal curve from said plurality of primary signal curves and said plurality of secondary signal curves.

9. The non-contact tonometer according to claim 8, wherein said detector array is a four-by-four array having sixteen photodiode elements.

10. The non-contact tonometer according to claim 9, wherein there are sixteen primary signal curves and thirty-three secondary signal curves.

11. The non-contact tonometer according to claim 1, wherein said applanation detection means further includes a beam contractor in front of said detector array.

12. The non-contact tonometer according to claim 1, wherein said applanation detection means further includes a lens array and an associated pinhole aperture array in front of said detector array.

13. The non-contact tonometer according to claim 11, wherein said applanation detection means further includes a lens array and an associated pinhole aperture array between said beam contractor and said detector array.

* * * * *